United States Patent [19]
Austin et al.

[11] Patent Number: 5,286,065
[45] Date of Patent: Feb. 15, 1994

[54] RETAINER ASSEMBLY FOR SYRINGE TIP

[75] Inventors: George K. Austin, Newberg; Sandor Johannes, West Linn; Ronald A. Rolleston, II, McMinnville, all of Oreg.

[73] Assignee: A-Dec, Inc., Newberg, Oreg.

[21] Appl. No.: 841,598

[22] Filed: Feb. 24, 1992

Related U.S. Application Data

[63] Continuation-in-part of Ser. No. 659,759, Feb. 22, 1991, abandoned.

[51] Int. Cl.$^5$ ............................................. F16L 55/00
[52] U.S. Cl. ........................................ 285/23; 285/93; 285/323; 285/133.1
[58] Field of Search ............... 285/322, 323, 23, 93, 285/342, 351, 133.1

[56] References Cited

U.S. PATENT DOCUMENTS

| | | | |
|---|---|---|---|
| Re. 20,704 | 4/1938 | Pieper | 219/39 |
| D. 316,600 | 4/1991 | Austin, Jr. et al. | D24/14 |
| 1,313,861 | 8/1919 | Reid et al. | |
| 1,958,332 | 5/1934 | Carpenter | 128/257 |
| 1,958,786 | 5/1934 | Eastman | 284/18 |
| 2,029,734 | 2/1936 | Meitzler | 128/257 |
| 2,517,689 | 8/1950 | Lement | 285/323 X |
| 2,571,856 | 10/1951 | Freedman | 32/33 |
| 3,121,426 | 2/1964 | Yoshida | 128/224 |
| 3,137,297 | 6/1964 | Maurer et al. | |
| 3,254,646 | 6/1966 | Staunt et al. | 128/224 |
| 3,391,696 | 7/1968 | Woodward | 128/232 |
| 3,563,575 | 2/1971 | Sanford | 285/323 |
| 4,026,025 | 5/1977 | Hunt | 32/22 |
| 4,113,284 | 9/1978 | Blocker | 285/93 X |
| 4,222,673 | 12/1983 | Blackford et al. | 285/23 |
| 4,248,589 | 2/1981 | Lewis | 433/80 |
| 4,249,899 | 2/1981 | Davis | 433/32 |
| 4,299,221 | 11/1981 | Phillips et al. | 128/276 |
| 4,340,365 | 7/1982 | Pisanu | 433/80 |
| 4,531,912 | 7/1985 | Schuss et al. | 433/80 |
| 4,531,913 | 7/1985 | Taguchi | 433/80 |
| 4,602,906 | 7/1986 | Grünenfelder | 433/80 |

(List continued on next page.)

OTHER PUBLICATIONS

A-Dec 117-page equipment catalog, cover and pp. 104, 105, 108, and 109, Jan. 1991.
Signo "Grand" 19-page Japanese language brochure, cover and p. 15, circa Jan. 1991.
A-Dec "J-Dec" two-page Japanese language brochure circa Jan. 1991.
Robin Dental Company 40-pg. catalog, cover and p. 35, Feb. 1985.
Marus Dental Equipment 40-page catalog, cover and pp. 24–25, Mar. 1982.
Planmeca Oy one-page "PM 2002 EC" brochure, circa Jan. 1991.
A-Dec "Continental System" two-page brochure circa Jan. 1991.
Osada "FX Series" 31-page Japanese language brochure, cover and pp. 25–27, circa Jan. 1991.

(List continued on next page.)

Primary Examiner—Dave W. Arola
Attorney, Agent, or Firm—Klarquist Sparkman Campbell Leigh & Whinston

[57] ABSTRACT

A syringe tip is connected to a syringe head by an assembly that permits quick detachment and replacement of syringe tips without the use of tools. The assembly is adjustable for permitting or restricting rotation of syringe tip.

10 Claims, 4 Drawing Sheets

U.S. PATENT DOCUMENTS

| | | | |
|---|---|---|---|
| 4,706,847 | 11/1987 | Sankey et al. | 222/1 |
| 4,784,649 | 11/1988 | Imonti et al. | 604/240 |
| 4,826,431 | 5/1989 | Fujimura et al. | 433/29 |
| 4,886,452 | 12/1989 | Löhn | 433/32 |
| 4,902,225 | 2/1990 | Löhn | 433/80 |
| 4,973,246 | 11/1990 | Black et al. | 433/32 |
| 4,975,054 | 12/1990 | Esrock | 433/80 |
| 4,993,948 | 2/1991 | Cameron et al. | 433/90 |
| 5,033,961 | 7/1991 | Kandler et al. | 433/89 |
| 5,049,071 | 9/1991 | Davis et al. | 433/80 |
| 5,150,880 | 9/1992 | Austin, Jr. et al. | 251/149 |

OTHER PUBLICATIONS

Dentech 32-page catalog, cover and p. 21, circa Jan. 1991.

Siemens 27-page catalog, cover and pp. 4 (including open flap), 10 and 11, Feb. 1991.

J. Morita Corporation "Surpass" 21-page Japanese language brochure, cover and pp. 18–19, circa Jan. 1991.

Elan 2000 III 20-page Japanese language catalog, cover and p. 16, circa Jan. 1991.

A-Dec Autoclavable Syringe installation instructions four-page pamphlet, Jan. 1991.

A-Dec Continental and Soft Touch Syringe installation instructions four-page pamphlet, Jan. 1991.

A-Dec Continental and Soft Touch Syringe Valve installation instructions two-page pamphlet, Jan. 1991.

A-Dec Syringe Tip Retainer Assembly installation instructions two-page pamphlet, Jun. 1991.

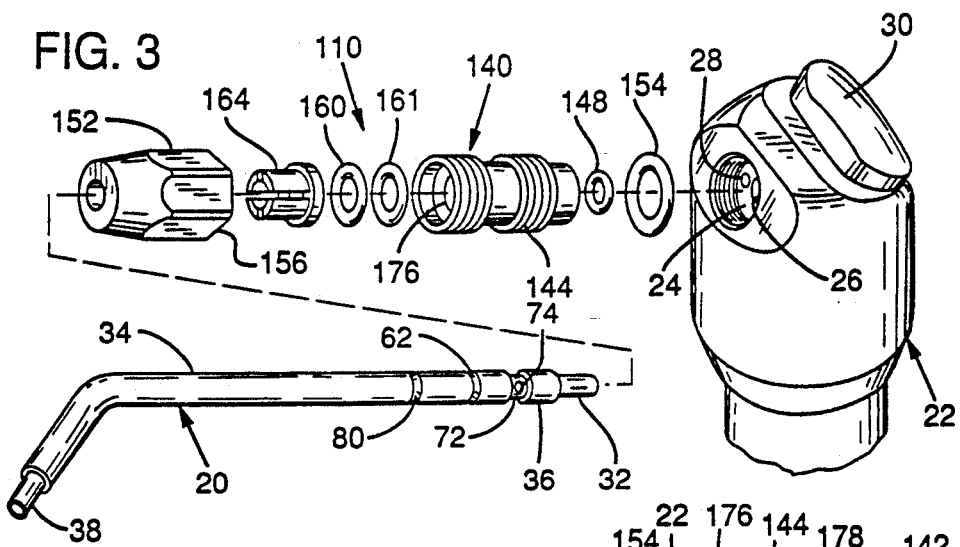
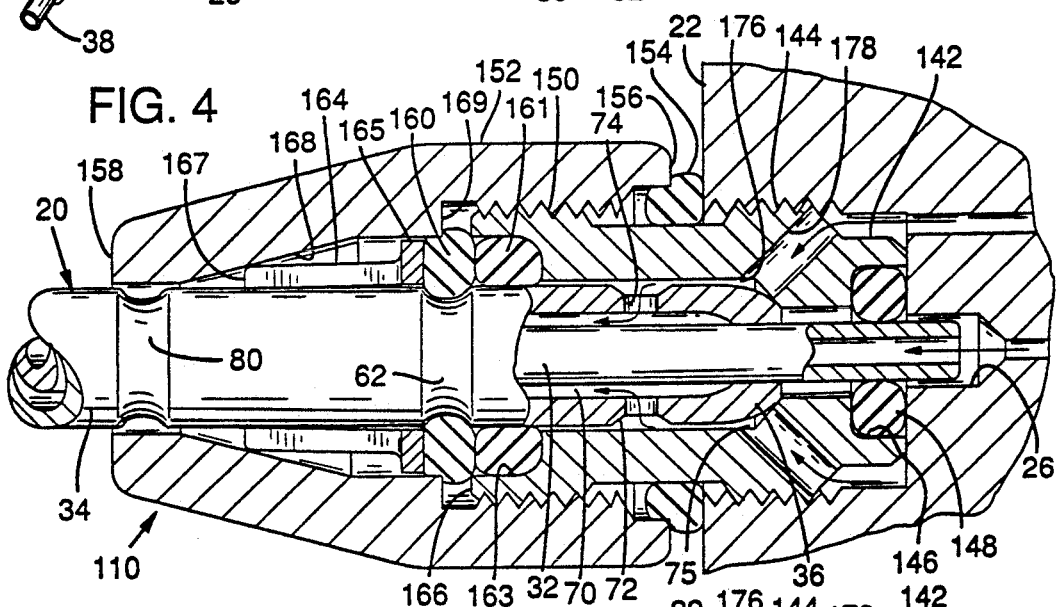
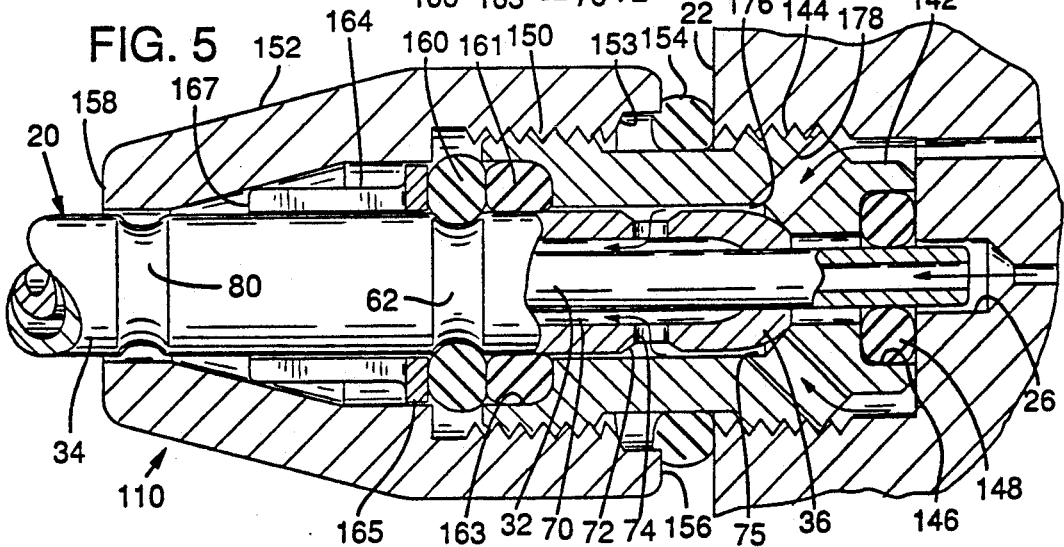

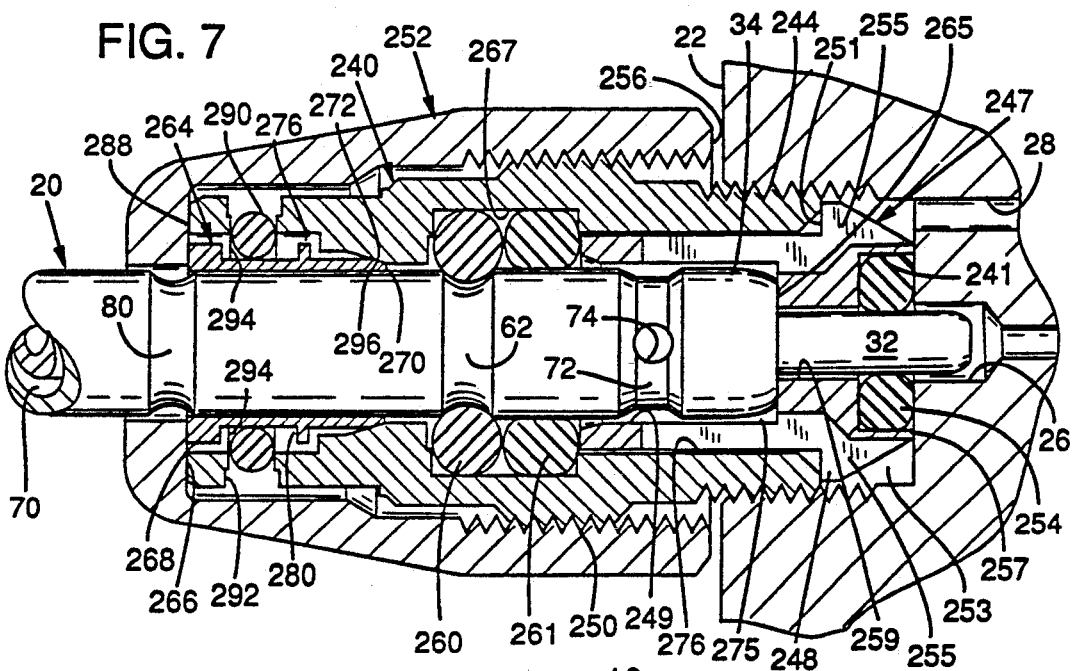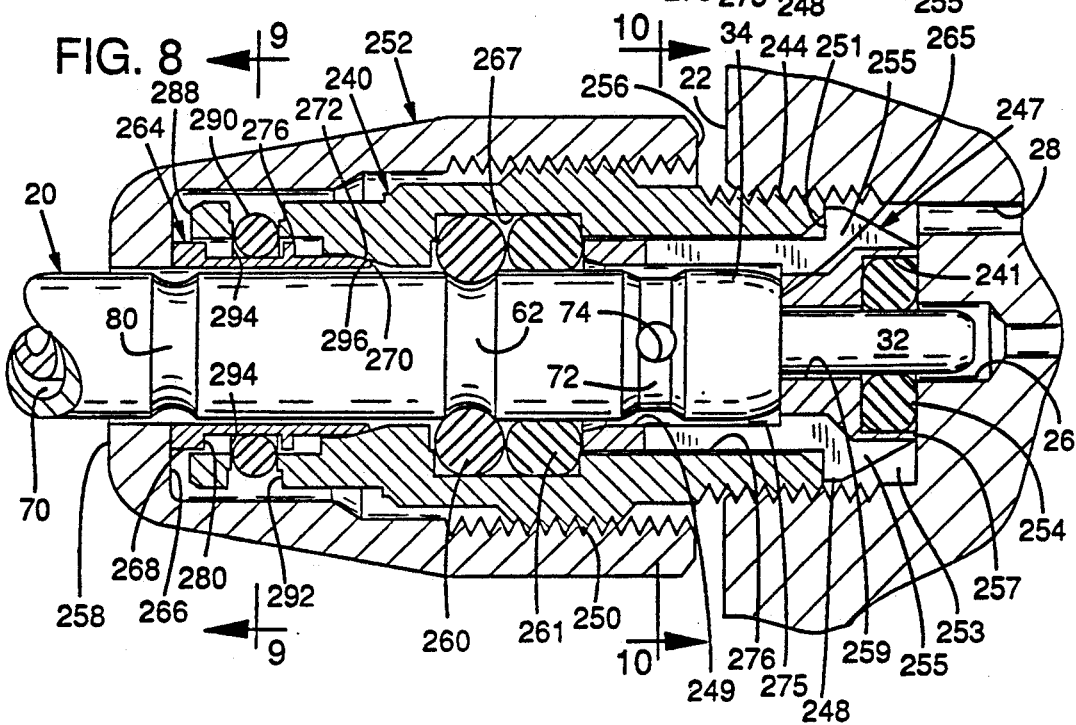

RETAINER ASSEMBLY FOR SYRINGE TIP

This is a continuation-in-part of U.S. patent application No. 07/659,759, filed Feb. 22, 1991 and now abandoned.

TECHNICAL FIELD

The present invention relates to an assembly for attaching a syringe tip to a syringe head.

BACKGROUND AND SUMMARY OF THE INVENTION

A syringe is used in dentistry for controlled delivery of liquid, air, or a combination of liquid and air, to the mouth of the patient. A syringe generally includes a syringe head that is manipulated by the operator and connected by flexible conduits to a source of water and compressed air. A tubular, elongated syringe tip is connected to the syringe head.

A conventional syringe tip comprises an inner tube and a concentric outer tube. The inner tube mates at one end with a liquid-outlet port in the syringe head, thereby providing a conduit for the liquid from the syringe head to the free end of the syringe tip.

The outer tube of the syringe tip has an inside diameter that is slightly greater than the outside diameter of the inner tube, thereby defining between the inner and outer tubes an annular air delivery chamber extending along the length of the syringe tip. The outer tube of the syringe tip joins the inner tube at the tip end that connects to the syringe head. At that end, the air delivery chamber is substantially closed, except for an air-inlet port in the outer tube that connects that chamber with an air-outlet port in the syringe head. Air flows out of the air delivery chamber at the free end of the syringe tip.

The operator controls the flow of liquid or gas through the syringe tip by operating valves that are mounted in the syringe head.

Syringe tips are disinfected after use with a single patient. Consequently, the mechanism employed for connecting the syringe tips to a syringe head should provide for quick and simple replacement of syringe tips while ensuring an effective seal between the syringe head and the connected syringe tip.

FIGS. 1 and 2 depict a prior art syringe tip assembly 10 for connecting a syringe tip 20 to a conventional syringe head 22. The syringe head 22 includes a threaded aperture 24, the innermost end of which aperture is in a fluid communication with a liquid-outlet port 26 and an air-outlet port 28 formed in the head 22. The liquid-outlet port 26 is connected to a flexible conduit (not shown) that extends from the syringe head 22 to a source of liquid, such as water. Similarly, the air-outlet port 28 is connected to a flexible conduit that connects the syringe head 22 with a source of compressed air. The liquid-outlet port 26 and the air-outlet port 28 are opened and closed by internal valves. A three-position button 30 is manipulated by the operator to control the valves.

The syringe tip 20 includes an elongated inner tube 32 and a concentric outer tube 34. The syringe tip 20 has a connecting end 36 that connects to the syringe head 22, and a free end 38 from which the liquid and air are expelled.

The connecting end 36 of the syringe tip fits into one end of a generally tubular coupler 40. The coupler 40 has near its innermost end 42 a threaded portion 44 that threads into the threaded aperture 24 in the syringe head 22.

At the connecting end 36 of the syringe tip 20, the inner tube 32 protrudes from the outer tube 34 to fit within the liquid-outlet port 26 in the syringe head. An annulus 46 is formed to protrude from the innermost end 42 of the coupler 40. An O-ring 48 fits inside the annulus 46. The annulus 46 and O-ring 48 are sized so that the O-ring 48 is firmly compressed against the syringe head 22 and around the portion of the inner tube 32 that protrudes from the outer tube 34 (FIG. 2). The O-ring 48, therefore, seals the connection between the liquid-outlet port 26 and the inner tube 32.

The end 66 of the coupler 40 that is opposite the annulus 46 carries external threads 50 for receiving a retainer nut 52 through which nut the syringe tip 20 extends as described below. A smooth portion of the exterior wall of the coupler 40 between the threaded portions 44, 50 carries an O-ring 54 for sealing the annular space between the retainer nut 52 and syringe head 22 whenever the nut 52 is tightened to the coupler 40.

The retainer nut 52 is a hollow, generally frustum shaped member having an inner end 56 and an outer end 58. The interior of the inner end 56 of the retainer nut 52 is threaded to engage the threads 50 on the coupler 40. Part of the outer surface of the inner end 56 is hexagonal in cross-section to receive a wrench for tightening the retainer nut 52 to the coupler 40.

Whenever the retainer nut 52 is tightened to the coupler 40 with the connecting end 36 of the syringe tip 20 in place (FIG. 2), a locking O-ring 60, which fits inside the retainer nut 52, is firmly compressed between a tapered sleeve 64 and the outer end 66 of the coupler 40 so that the locking O-ring 60 is forced into an annular recess 62 formed in the outer surface of the outer tube 34.

More particularly, the outer surface 67 of the tapered sleeve 64 tapers outwardly (i.e., to the left in FIG. 2) and bears against a correspondingly tapered surface 68 defined by the inside wall of the retainer nut 52. The locking O-ring 60 is located between the tapered sleeve 64 and the outer end 66 of the coupler 40. As a result, whenever the retainer nut 52 is threaded onto the coupler 40, the tapered sleeve 64 is forced against the locking O-ring 60, compressing the ring 60 as mentioned above, thereby securing the syringe tip 20 to the coupler 40 (hence, to the syringe head 22).

The outer tube 34 is crimped to the inner tube 32 at connecting end 36 to close the end of the air delivery chamber 70 that is defined between the outer tube 34 and the inner tube 32. An annular recess 72 is formed near the crimped end. Two or more inlet ports 74 are formed through the outer tube 34 at the recess 72. An air passage 75 is defined between the outer surface of the tube 34 and the inner wall 76 of the coupler 40 at the crimped end of the outer tube 34. This air passage 75 is in fluid communication with the air-outlet port 28 in the syringe head 22 via holes 78 in the innermost end 42 of the coupler 40.

The just described prior art syringe tip assembly 10 is designed so that the retainer nut 52 must be securely fastened to the coupler 40 in order to retain the syringe tip 20 in place. Accordingly, it is necessary to employ a tool for loosening the retainer nut 52 to permit removal of the syringe tip 20. In loosening the retainer nut 52, the nut may be backed completely off the threads 50 of the coupler 40, which can lead to the separation and loss of internal parts, such as the tapered sleeve 64 and the locking O-ring 60.

In some dental procedures it is desireable to secure the tip 20 to the syringe head 22 so that it is irrotatable about its longitudinal axis. Such an irrotatable syringe tip may be desirable, for example, when the tip 20 is used for retracting the cheek of a patient. The tip must be secured against rotation because the retraction force applied to the bent free end of the tip 20 tends to rotate the tip within the coupler 40. The prior art syringe tip assembly 10 just described is designed so that the compressed locking O-ring 60 normally secures the tip 20 to be irrotatable about its longitudinal axis.

In other applications, a rotatable syringe tip is preferred. The tip 20 can be made rotatable by loosening the retainer nut 52, thereby permitting the locking O-ring 60 to resile and reduce the force applied by the O-ring to the outer tube 34. By loosening the retainer nut 52, however, it is possible that subsequent rotation of the syringe tip 20 will be transferred via the O-ring 60 to the retainer nut 52, which can eventually unthread the retainer nut 52 and cause the tip 20, retainer nut 52, and internal parts to fall from the syringe head 22.

In the past, split collets have been available for replacing the tapered sleeve 64 mentioned above. The force of the retainer nut interior surface 68 against the split collet tightens the collet 64 to the tip 20 to restrict tip rotation. The collet, however, may be lost in the event that the retainer nut 52 is loosened as described above.

This invention is directed to an assembly for connecting a syringe tip to a syringe head and provides for rapid replacement of the syringe tip. In many applications, the need for a tool to loosen the connection is eliminated.

The assembly is adjustable for permitting or prohibiting rotation of the syringe tip about its longitudinal axis. In one embodiment, the assembly is configured so that rotation of the tip can not unthread the retainer nut from the coupler. In another embodiment, the assembly is configured so that individual components (collet and O-rings) are not free to fall from the coupler even though the retainer nut is removed.

As another aspect of this invention, the assembly is constructed so that it may be used with existing syringe heads.

BRIEF DESCRIPTION OF THE DRAWINGS

FIG. 3 is an exploded, perspective view of a syringe tip retainer assembly formed in accordance with the present invention.

FIG. 4 is an enlarged, cross-sectional view showing the assembly of FIG. 3 connected to a syringe head and adjusted for restricting rotation of the syringe tip.

FIG. 5 is a cross-sectional view of the assembly of FIG. 3 connected to a syringe head and adjusted for permitting rotation of the syringe tip.

FIG. 7 is an cross-sectional view showing the alternative retainer assembly of FIG. 6 connected to a syringe head and adjusted for restricting rotation of the syringe tip.

FIG. 8 is a cross-sectional view of an alternative retainer assembly connected to a syringe head and adjusted for permitting rotation of the syringe tip.

DETAILED DESCRIPTION OF PREFERRED EMBODIMENTS

Figure 1:
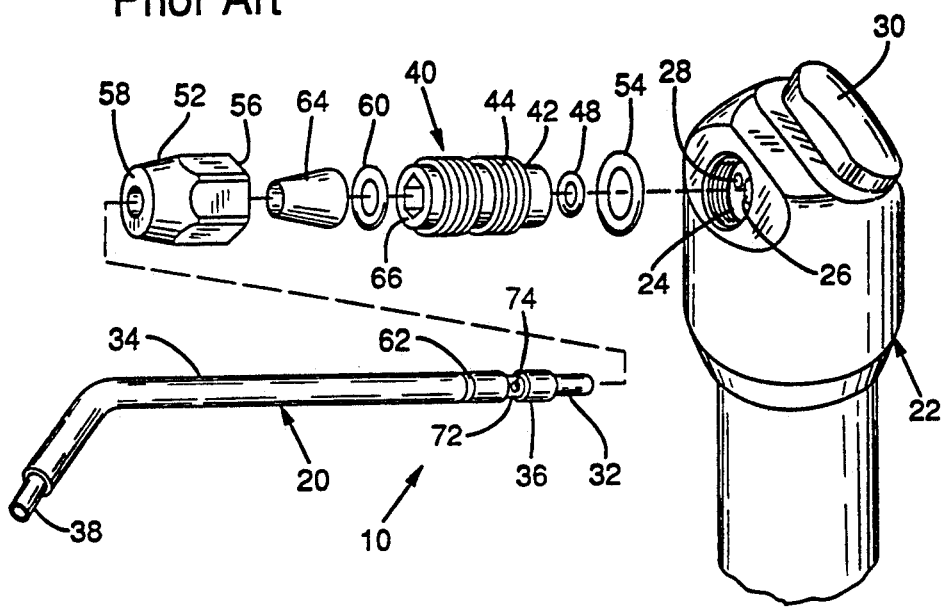
FIG. 1 is an exploded, perspective view of a prior art assembly for attaching a syringe tip to a syringe head.
Figure 2:
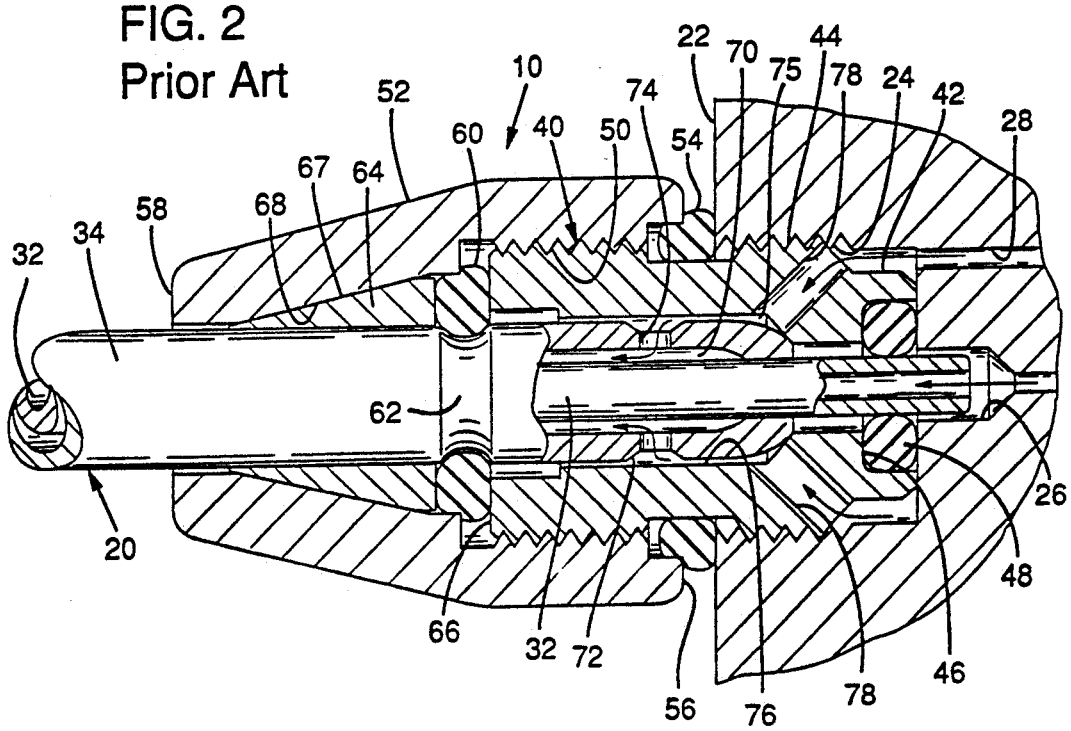
FIG. 2 is an enlarged cross-sectional view showing the prior art assembly connected to a syringe head.

A syringe tip retainer assembly 110 of the present invention (FIGS. 3–5) is employed for connecting a syringe tip 20 to a conventional syringe head 22. The syringe tip 20 and syringe head 22 depicted in FIGS. 3–5 are, unless otherwise noted below, the same as those described with respect to the prior art mechanisms depicted in FIGS. 1 and 2. Accordingly, identical reference numerals will be employed for representing identical elements in the syringe tip 20 and head 22. The presently described assembly 110 and the alternative assembly 210 (FIGS. 6–10) are useful with existing syringe tip and syringe head designs without the need for modifying those components.

The assembly 110 includes a generally tubular coupler 140. The coupler 140 has near its innermost end 142 a threaded portion 144 that threads into the threaded aperture 24 in the syringe head 22. To this end, the interior surface 176 of the coupler 140 is shaped to engage an Allen wrench that can be extended into the coupler 140 before the syringe tip 20 is inserted therethrough.

An annulus 146 is formed to protrude from the innermost end 142 of the coupler 140. An O-ring 148 fits inside the annulus 146. The annulus 146 and O-ring 148 are sized so that the O-ring 148 is firmly compressed against the syringe head 22 and around the portion of the syringe tip inner tube 32 that protrudes from the outer tube 34 (FIG. 4). The O-ring 148, therefore, seals the connection between the liquid-outlet port 26 and the inner tube 32.

The end 166 of the coupler 140 that is opposite the annulus 146 carries external threads 150 for receiving a retainer nut 152 through which nut the tip 20 passes as described below. A smooth portion of the exterior wall of the coupler 140 between the threaded portions 144, 150 carries an O-ring 154 for sealing the annular space between the retainer nut 152 and syringe head 22.

The outer end 166 of the coupler 140 has an annular recess 163 formed therein for carrying a keeper O-ring 161. The keeper O-ring 161 and recess 163 are sized so that the ring 161 is continuously compressed against the syringe tip 20 that is inserted into the syringe head 22. The keeper O-ring 161 also serves to improve the seal between the syringe tip outer tube 34 and the interior surface 176 of the coupler 140 so that air in the passage 75 will be directed through the holes 178 in coupler 140 and into the air delivery chamber 70 of the syringe tip.

The retainer nut 152 is a hollow, generally frustum shaped member having an inner end 156 and an outer end 158. The interior of the inner end 156 of the retainer nut 152 is threaded to engage the outer threads 150 on the coupler 140. Part of the outer surface of the inner end 156 is hexagonal in cross-section for receiving a wrench to adjust the assembly 110 as described below.

The retainer nut 152 is movable relative to the coupler 140 between a locked position (FIG. 4) and an unlocked position (FIG. 5). In the locked position, the retainer nut 152 is advanced on the threads 150 of the coupler in a manner such that the tapered interior surface 168 of the retainer nut 152 bears upon a split collet 164 that surrounds the syringe tip 20. The collet 164 is forced by the advancing retainer nut 152 toward the outer end 166 of the coupler 140. As a result, a flanged end 165 of the split collet 164 bears upon a locking O-ring 160 that is located between the flanged end 165 and the keeper O-ring 161 and that fits within the annular recess 62 in the syringe tip whenever the syringe tip is inserted into the syringe head 22.

To ensure that a syringe tip is properly connected to the syringe head 22, an indicium 80 is placed on the syringe tip 20 near the connecting end 36 of the tip. The indicium 80 is located so that whenever the tip 20 is properly connected to the syringe head 22 (that is, whenever the locking O-ring 160 is received within the recess 62 of the tip) the indicium 80 will be adjacent to the outer end 158 of the retainer nut 152.

Preferably, the indicium 80 comprises a annular groove formed in the outer tube 34 of the syringe tip 20. The indicium 80 is located relative to the recess 62 so that the indicium will be obscured from the user's view just inside the outer end 158 of the retainer nut 152 whenever the tip is properly connected. Put another way, the user connects the syringe tip to the head by pushing the tip inwardly (to the right in FIG. 4) until the indicium 80 is no longer visible.

The force of the collet 164 against the locking O-ring 160 and against the adjacent keeper O-ring 161 compresses those rings 160, 161 against the outer surface of the syringe tip 20 for restricting rotation of the syringe tip about its longitudinal axis. Moreover, as the movement of the split collet 164 along the tip 20 is resisted by the compressed rings 160, 161, the outermost end 167 of the collet 164 is squeezed against the syringe tip 20 by the retainer nut 152 as the nut 152 is moved into the locked position (FIG. 4). The collet 164, therefore, increases the rotational resistance applied to the syringe tip 20. Hand-tightening of the retainer nut 152 provides sufficient force to the collet 164 so that the collet 164 prevents removal of the tip 20 from the head 22 unless the retainer nut 152 is thereafter loosened.

It is noteworthy that as the retainer nut 152 moves toward the locked position, an internal shoulder 169 formed in the nut 152 moves across part of the radially outer surface of the locking O-ring 160 to limit expansion of the locking O-ring 160 (as the O-ring 160 is compressed by the collet 164) away from the syringe tip, which expansion would otherwise reduce the force of the O-ring 160 against the tip 20.

As noted, the syringe tip 20 is held by the collet 164, locking O-ring 160, and keeper O-ring 161 against rotation whenever the assembly 110 is in the locked position. If desired, the retainer nut 152 can be tightened into the locked position by applying a wrench to the hexagonal surface portion of the outer surface of the retainer nut 152.

The unlocked position (FIG. 5) into which the assembly 110 may be adjusted not only permits rotation of the syringe tip 20 about its longitudinal axis, but also allows quick disconnection and reconnection of the syringe tip 20 without the use of tools. In this regard, the retainer nut 152 is partly unthreaded from the coupler 140, thereby reducing the force applied by the collet 164 to both the locking O-ring 160 and to the syringe tip 22. Specifically, as the retainer nut 152 is moved to the unlocked position, the force of the tapered interior surface 168 of the retainer nut 152 against the outermost end 167 of the collet 164 is substantially eliminated, thereby relieving the force of the split collet 164 acting on the locking O-ring 160 and against the syringe tip 20.

During manufacture of the assembly 110, the outermost one 153 of the retainer nut threads 150 is deformed after the retainer nut 152 is threaded onto the coupler 140. As a result, the retainer nut 152 can not be threaded off the coupler 140 as the retainer nut is moved to the unlocked position. The effect of this irremovable attachment of the retainer nut 152 to the coupler 140 is to eliminate the possibility of losing the small internal parts (collet 164 and O-rings 160, 161, 154) of the assembly 110, which loss might otherwise occur if the nut 152 could be completely removed from the coupler 140.

With the retainer nut 152 in the unlocked position (FIG. 5), the locking O-ring 160 and the keeper O-ring 161 keep the syringe tip 20 attached to the coupler 140 until the tip is manually removed for the purpose of replacing the tip. Accordingly, the syringe tip 20 can be quickly and easily replaced by hand whenever the retainer nut is out of the locked position (FIG. 4).

FIGS. 6-10 depict an alternative embodiment of a syringe tip retainer assembly 210 formed in accordance with the present invention. The alternative assembly 210 includes a generally tubular coupler 240. The coupler 240 has near its innermost end a threaded portion 244 that threads into the threaded aperture 24 in the syringe head 22. To this end, the otherwise generally cylindrical outer surface of the coupler 240 has formed in it a pair of opposing parallel flats 245, against which flats a wrench may be employed for rotating the coupler 240 when tightening the coupler 240 into the aperture 24.

A spacer 247 makes up part of the assembly 210 and is installed between the inner end 242 of coupler 240 and the syringe head 22. Generally, the spacer 247 provides a seat against which the coupler 240 is tightened, and defines an air path for conducting air from the air-outlet port 28 into the air passage 275 that is defined between the outer surface of the syringe tip outer tube 34 and the inner surface 276 of the inner end of the coupler 240. As was the case with the prior described embodiment, air in the passage 275 is directed through inlet ports 74 in the syringe tip and through chamber 70 to pass from the free end 38 of the tip.

More particularly, the spacer 247 is a generally cylindrical component having an outer end portion 249 of constant diameter that fits inside the inner end 242 of the coupler 240. The spacer 247 has a flanged inner end 248. The outside diameter of the flanged end 248 of the spacer 247 is just slightly less than the diameter of the threaded aperture 24. The flanged end 248 defines a shoulder 251 against which the inner end 242 of the coupler 240 seats when the coupler is threaded into the aperture 24.

The flanged end 248 of the spacer is tapered inwardly; that is, so that the outside diameter of the flanged end generally decreases in the direction toward the syringe head 22. This tapered surface of the spacer flanged end 248 defines an annular chamber 253 between the installed spacer 247 and the air-outlet port 28 so that air can flow out of that port 28 and into chamber 253.

The spacer has two, spaced apart, elongated slots 255 extending from the flanged end 248 to a location near the outermost part of the outer end 249 of the spacer. Slots 255 in the spacer 255 provide an air path between the annular chamber 253 and the air passage 275 at the connected end of the syringe tip.

Slightly away from the innermost portion 257 of the spacer flanged end 248, the bore 259 of the spacer has a diameter that is just slightly larger than that of the exposed inner tube 32 at the connecting end 36 of the syringe tip. The bore is enlarged to define an annular recess 263 in the innermost portion 257 of the spacer to accommodate an O-ring 254 that fits snugly inside the recess 263.

The diameter of the bore 259 is stepped to define in the outer end 249 of the spacer an internal shoulder 265 against which the innermost end of the outer tube 34 abuts when the syringe tip is fully inserted into the syringe head 22.

The bore of the coupler 240 has a central portion 267 that has a relatively greater diameter than the remaining portion of the coupler bore. The central portion 267 of the coupler bore carries a locking O-ring 260 and an adjacent keeper O-ring 261. The keeper O-ring 261 and bore portion 267 are sized so that the keeper O-ring ring 261 is continuously compressed against the syringe tip 20 that is inserted to the syringe head 22. The keeper O-ring 261 also serves to provide a seal between the syringe tip outer tube 34 and the inner surface 276 of the inner end of the coupler 240 so that air will not leak from the air passage 275.

The locking O-ring 260, which is also retained within the bore portion 267, is compressed between the radially outermost surface of the bore portion 267 and the syringe tip 20 when the syringe tip is inserted. As with the prior-described locking O-ring 160, the O-ring 260 is oriented so that it is forced into the annular recess 62 formed in the outer surface of the syringe tip outer tube 34 whenever the tip is inserted into the syringe head.

The coupler 240 carries a split collet 264 that can be tightened against the syringe tip 20 as a retainer nut 252 is threaded over the coupler 240. Turning first at the particulars of the retainer nut 252, that nut is a hollow, generally frustum-shaped member having an inner end 256 and an outer end 258. The interior of the inner end 256 of the retainer nut 252 is threaded to engage a raised, threaded portion 250 formed at the central portion of the outside of the coupler 240.

Part of the outer surface of the retainer nut inner end 256 is hexagonal in cross-section for receiving a wrench, thereby to thread the retainer toward or away from the syringe head for respectively tightening or loosening the split collet 264 against the syringe tip.

The outer end 258 of the retainer nut defines an internal shoulder 266 that bears against the split collet 264 when the retainer nut is tightened, as described more fully below.

Figure 6:
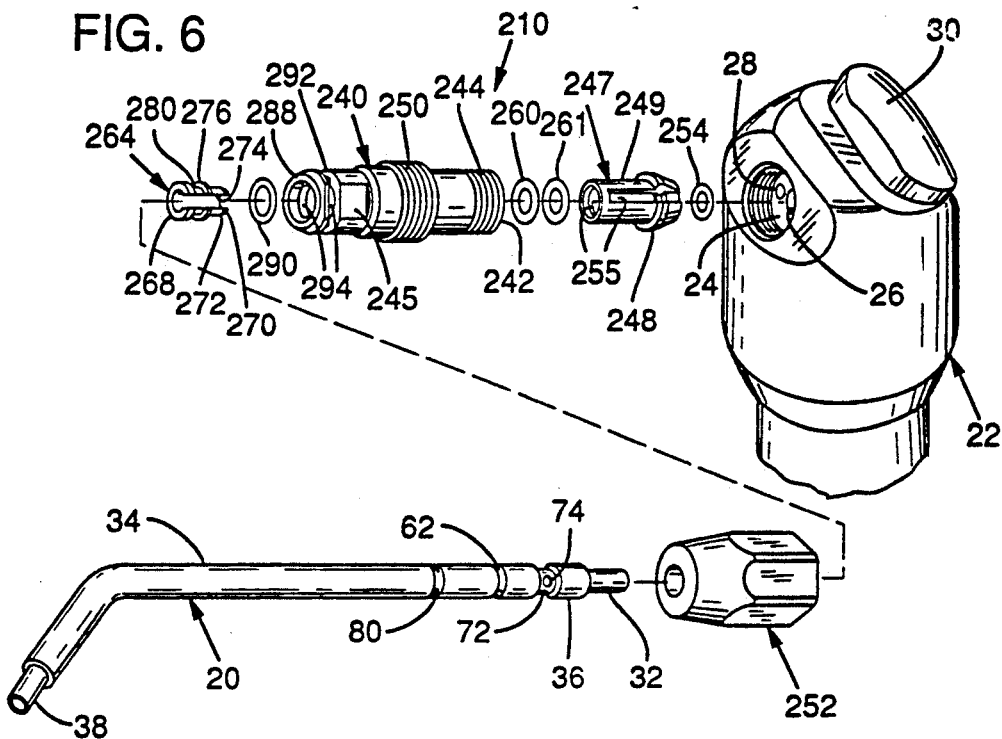
FIG. 6 is an exploded, perspective view of an alternative retainer assembly in accordance with the present invention.
Figure 9:
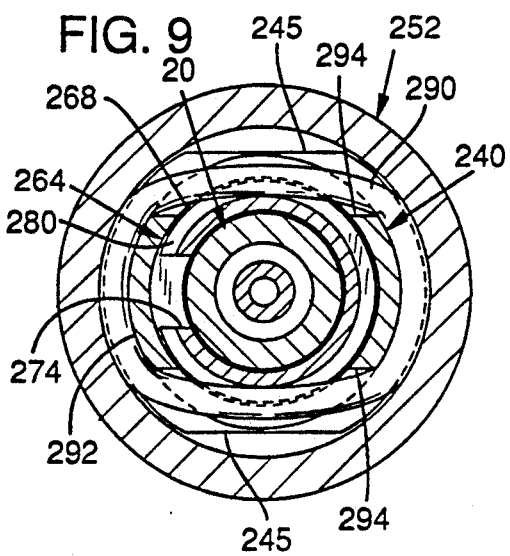
FIG. 9 is a cross-sectional view of the alternative retainer assembly taken along line 9—9 of FIG. 8.
Figure 10:
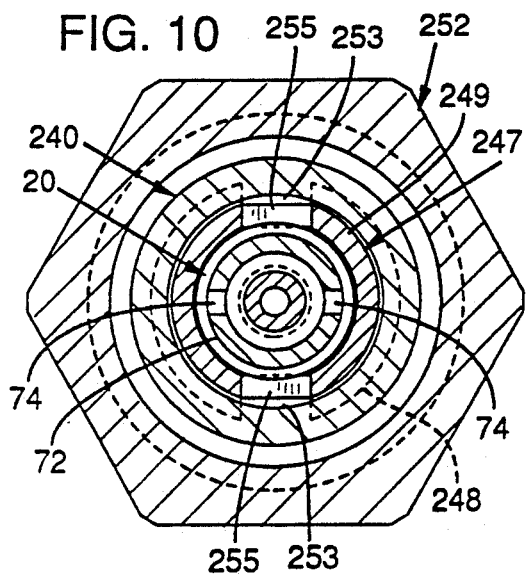
FIG. 10 is a cross-sectional view of the alternative retainer assembly taken along line 10—10 of FIG. 8.

The split collet 264 is a generally tubular member having a flanged outer end 268 and an inner edge 270 that has beveled outer surface 272. The split 274 in the collet 264 extends completely through the collet, as best shown in FIG. 6. Between the inner edge 270 and the flanged end 268 of the collet is a radially protruding lip 276 formed integrally with the collet. The lip 276 and the flanged end 268 of the collet define between them a channel 280 that extends completely around the circumference of the collet (except for the split).

The coupler 240 carries on its outer end 288 a holder O-ring 290 that protrudes into the channel 280 and prevents the collet from falling from the coupler 240 when the syringe tip or retainer nut 252 is removed. More particularly, a circumferential recess 292 is formed in the coupler 240 at a location spaced away from the outermost end 288 of the coupler. Openings 294 are cut at diametrically opposed regions of the recess bottom surface so that along the circumferential length of those openings 294, the recess opens into the bore of the coupler as best seen in FIG. 6.

The resilient holder O-ring 290 fits within the coupler recess 292 with sufficient tension to cause the portions of the holder O-ring that span the openings 294 in the coupler to extend through those openings into the bore of the coupler.

The bore of the coupler 240 near the outer end 288 is shaped to receive therein the split collet 264 so that the portions of the holder O-ring 290 that protrude through the openings 294 in the coupler recess 292 extend into the channel 280 that is defined by the radially protruding lip 276 and flanged end 268 of the split collet as shown in FIGS. 7 and 8.

As a result of the construction just described, it will be appreciated that the retainer nut 252 may be completely removed (that is, unthreaded) from the coupler 240, and the holder O-ring 290 will hold the collet 264 in place within the bore of the outer end 288 of the coupler 240. Moreover, because the keeper O-ring 261 and locking O-ring 260 fit tightly within the central portion 267 of the coupler bore, removal of the retainer nut 252 will not cause those O-rings to fall from the assembly.

The retainer nut 252 is movable relative to the coupler 240 between a locked position (FIG. 7) and an unlocked position (FIG. 8). It is noteworthy that, away from the openings 294, the holder O-ring contacts the retainer nut 252. The effect of this frictional contact is to resist rotation of the retainer nut so that the nut is unlikely to become inadvertently unthreaded (e.g., through vibration) from the coupler.

In the locked position, the retainer nut 252 is advanced over the threads 250 of the coupler in a manner such that the interior shoulder 266 of the retainer nut bears against the flanged end 268 of the split collet 264 that surrounds the inserted syringe tip. The split collet 264 is forced by the retainer nut shoulder 266 toward the syringe head so that the beveled outer surface 272 of the collet inner edge 270 bears against a tapered portion 296 of the coupler bore in a manner such that the resultant force of the advancing collet against the coupler pushes the split collet 264 tightly against the outer tube 34 of the syringe tip. In the locked position, the syringe tip is held by the collet 264 against rotation about the longitudinal axis of the syringe tip.

Preferably, the coupler is sized so that the outer end 288 of the coupler will contact the shoulder 266 of the retainer nut to prohibit further advance of the retainer nut 252 against the collet 264 as the collet reaches the location where the collet is forced firmly against syringe tip, but not so firmly as to damage the tip. Put another way, the coupler 240 is configured to form a stop for further advance of the retainer nut 252, thereby limiting the force that can be applied by the collet 264 to the syringe tip 20.

As in the prior embodiment, an indicium 80 is placed on the syringe tip 20 near the connecting end 36 of the tip so that whenever the tip is properly installed or connected to the syringe head (that is, whenever the locking O-ring 260 is received within the annular recess 62 on the tip), the indicium 80 will be adjacent to the outer end 258 of the retainer nut 252, obscured from view.

The unlocked position (FIG. 8), into which the assembly 210 may be adjusted by loosening of the retainer nut 252 permits rotation of the syringe tip 20 about its longitudinal axis and allows quick disconnection and reconnection of the tip without the use of tools, as was the case with prior embodiments. To this end, the retainer nut 252 is partly unthreaded from the coupler 240, thereby reducing the force applied by the collet 264 to the syringe tip 20.

In this embodiment, the coupler 240 is constructed so that the retain nut 252 can be completely removed from the coupler to provide access for replacing damaged or worn O-rings. It will be appreciated, however, that because of the effect of the holder O-ring 290, as describe above, removal of the retainer nut 252 (either intentional or inadvertent) will not cause loose parts to fall away from the assembly.

Having illustrated and described the principles of the invention in preferred embodiments, it should be apparent to those skilled in the art that the invention can be modified in arrangement and detail without departing from such principles. Accordingly, we claim all modifications coming within the spirit and scope of the following claims.

The invention claimed is:

1. An assembly for connecting a syringe tip to a syringe head, comprising:
   a tubular coupled having an inner end and an outer end and having a bore sized to permit a syringe tip to extend therethrough and means to seal a syringe tip to said coupler, the inner end being configured to be connectable to a syringe head;
   a collet member disposed near the outer end of the coupler and configured for surrounding a syringe tip that extends through the coupler, the collet member being slidable along a portion of a syringe tip it surrounds;
   a retainer element having means to engage said collet member and said retainer element and coupler having coacting means for removably attaching said retainer element to the coupler to allow said retainer element to be advanced and retracted on the coupler and to advance against the collet member for pushing the collet member against the coupler wherein said coupler and collet have coacting surface means thereon, thereby forcing the collet member against a surrounded syringe tip; and
   securing means for securing the collet member to and near the outer end of the coupler irrespective of movement of the retainer element relative to the coupler.

2. The assembly of claim 1 wherein the securing means comprises a ring carried by the coupler to surround the collet, the collet having a channel defined thereon into which channel part of the ring extends to limit the amount of movement of the collet relative to the coupler.

3. The assembly of claim 2 wherein the ring is a resilient member that contacts the retainer and that is removable from the coupler.

4. The assembly of claim 2 wherein the coupler includes a groove formed therein, in which groove the ring is carried, the coupler also having an opening formed therein between the groove and the bore, the ring protruding through the opening and into the bore to extend into the channel that is defined on the collet member.

5. The assembly of claim 1 further comprising stop means for stopping the advance of the retainer element on the coupler thereby to limit the amount that the collet member may be pushed by the retainer element.

6. The assembly of claim 1 further comprising a spacer member having one part that fits within the coupler bore and having another part that fits between the inner end of the coupler and the syringe head, the spacer being configured to define an air path between the syringe head and the bore of the coupler.

7. The assembly of claim 1 wherein said means to seal comprises a compressible member disposed inside the tubular coupler and sized to be compressed against a syringe tip that is extended through the coupler.

8. The assembly of claim 7 further comprising a second compressible member located adjacent to the first-mentioned compressible member and sized to fit within an annular groove formed in the exterior of a syringe tip that is extended through the coupler.

9. The assembly of claim 8 wherein the first-mentioned and second compressible members are carried within a recess formed in the bore of the coupler between the ends of the coupler.

10. The assembly of claim 1 wherein said coacting means between said retainer element.

* * * * *

UNITED STATES PATENT AND TRADEMARK OFFICE
CERTIFICATE OF CORRECTION

PATENT NO. : 5,286,065

DATED : February 15, 1994

INVENTOR(S) : George K. Austin, et al

It is certified that error appears in the above-indentified patent and that said Letters Patent is hereby corrected as shown below:

Column 7, line 21, "o-ring ring" should be --o-ring--.

In the Claims:

Column 9, line 30, "coupled" should be --coupler--;

Column 9, line 32, "therethrough" should be --therethrough,--; and

UNITED STATES PATENT AND TRADEMARK OFFICE
CERTIFICATE OF CORRECTION

PATENT NO. : 5,286,015

DATED : February 15, 1994

INVENTOR(S) : George K. Austin, et al

It is certified that error appears in the above-indentified patent and that said Letters Patent is hereby corrected as shown below:

Column 9, line 40, to column 10, line 1, "a retainer element having means to engage said collet member and said retainer element and coupler having coacting means for removably attaching said retainer element to the coupler to allow said retainer element to be advanced and retracted on the coupler and to advance against the collet member for pushing the collet member against the coupler wherein said coupler and collet having coacting surface means thereon," should be --a retainer element means for removably engaging the coupler in a manner to allow said retainer element means to be advanced and retracted on the coupler and to advance against the collet member for pushing the collet member against the coupler,--

Signed and Sealed this

Eighth Day of November, 1994

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO. : 5,286,065
DATED : February 15, 1994
INVENTOR(S) : George K. Austin et al.

It is certified that error appears in the above-indentified patent and that said Letters Patent is hereby corrected as shown below:

Column 10, line 5, after "element" add --means--.

Column 10, lines 33-34, please delete "wherein said means to seal comprises" and insert therefor --further comprising--.

Column 10, lines 46-47, after "wherein" please delete "said coacting means between said" and insert therefor --the--;

after "retainer element" insert --means is threaded to the coupler and wherein the securing means includes deformed thread means for preventing the retainer element means from being completely unthreaded from the coupler--.

Signed and Sealed this

Third Day of January, 1995

*Attest:*

BRUCE LEHMAN

*Attesting Officer*   *Commissioner of Patents and Trademarks*